(12) United States Patent
Grabmaier

(10) Patent No.: US 11,494,671 B2
(45) Date of Patent: Nov. 8, 2022

(54) PRECISION HYGIENE USING REINFORCEMENT LEARNING

(71) Applicant: Olivia Karen Grabmaier, Spardorf (DE)

(72) Inventor: Olivia Karen Grabmaier, Spardorf (DE)

(*) Notice: Subject to any disclaimer, the term of this patent is extended or adjusted under 35 U.S.C. 154(b) by 362 days.

(21) Appl. No.: 16/833,485

(22) Filed: Mar. 27, 2020

(65) Prior Publication Data

US 2021/0012224 A1      Jan. 14, 2021

Related U.S. Application Data

(60) Provisional application No. 62/967,683, filed on Jan. 30, 2020, provisional application No. 62/897,404, filed on Sep. 9, 2019, provisional application No. 62/873,956, filed on Jul. 14, 2019.

(51) Int. Cl.
| | |
|---|---|
| *G06N 3/00* | (2006.01) |
| *G06N 5/04* | (2006.01) |
| *G06N 20/00* | (2019.01) |
| *G06N 7/00* | (2006.01) |
| *G06N 5/02* | (2006.01) |
| *G06F 17/18* | (2006.01) |

(52) U.S. Cl.
CPC ............... *G06N 5/04* (2013.01); *G06N 20/00* (2019.01); *G06F 17/18* (2013.01); *G06N 5/02* (2013.01); *G06N 7/00* (2013.01)

(58) Field of Classification Search
CPC ............ G06N 20/00; G06N 5/04; G06N 5/03; G06N 5/02; G06N 7/00; G06F 17/18
See application file for complete search history.

(56) References Cited

U.S. PATENT DOCUMENTS

| | | | |
|---|---|---|---|
| 10,402,469 | B2 | 9/2019 | McMahan et al. |
| 10,657,461 | B2 | 5/2020 | McMahan et al. |
| 2017/0175172 | A1* | 6/2017 | Apte ................. G16B 50/20 |

FOREIGN PATENT DOCUMENTS

| | | |
|---|---|---|
| AU | 2017229488 A1 | 9/2018 |
| CA | 3016891 A1 | 9/2017 |
| CN | 108351881 A | 7/2018 |
| CN | 108699586 A | 10/2018 |
| EP | 3426794 A1 | 1/2019 |
| EP | 3494522 B1 | 6/2019 |
| WO | 2017066509 A1 | 4/2017 |
| WO | 2017156031 A1 | 9/2017 |
| WO | 2018057302 A1 | 3/2018 |

OTHER PUBLICATIONS

McMahan et al., "Federated Learning of Deep Networks using Model Averaging", arXiv:1602.05629v1, Feb. 17, 2016, 11 pages.
Bonawiiz et al., "Towards Federated Learning at Scale: System Design", arXiv:1902.01046v1, Feb. 4, 2019, 15 pages.

* cited by examiner

*Primary Examiner* — Joseph J Lauture

(57) ABSTRACT

Methods, systems, and apparatus, including computer programs encoded on computer storage media, for reinforcement learning in the field of hygiene. Specifically, the features described relate to selecting actions in a context to be performed by an agent that interacts with an environment by receiving observations, in response, performing actions from a set of actions, wherein the context comprises a bacterial product to be prescribed, wherein the observations comprise data from the mapping of applied bacteria, and wherein the actions comprise data for the prescription of the bacterial product.

20 Claims, 10 Drawing Sheets

PRECISION HYGIENE USING REINFORCEMENT LEARNING

CROSS-REFERENCE TO RELATED APPLICATIONS

This application claims the benefit of U.S. Provisional Application No. 62/967,683, filed on Jan. 30, 2020. This application claims the benefit of U.S. Provisional Application No. 62/897,404, filed on Sep. 9, 2019. This application claims the benefit of U.S. Provisional Application No. 62/873,956, filed on Jul. 14, 2019. The disclosure of each prior application is considered part of and is incorporated by reference in the disclosure of this application to the extent not inconsistent with the disclosure herein.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND

The present disclosure relates to reinforcement learning in the field of hygiene. More particularly, the disclosure relates to hygienic control of microbes on surface.

Generally, hygiene refers to techniques and procedures with the aim to control targeted microbes on the surface of living and non-living objects. The focus is on bacteria and viruses, which are the most common source of infection.

The term "subtractive hygiene" is defined as the use of antimicrobial techniques or products, for example, disinfectants, to control targeted microbes, comprising bacteria and viruses, on the surface. Subtractive hygiene aims to reduce or inhibit targeted microbes by using antimicrobial techniques or products that are biocidal or biostatic.

The term "additive hygiene" is defined as the use of bacterial products with harmless or beneficial character, for example, probiotics, to control targeted bacteria on the surface. Additive hygiene aims to reduce or inhibit targeted bacteria by using bacterial products that lead to competitive coexistence or exclusion.

The quantity of targeted bacteria, comprising pathogens, is the difference between the quantity of applied bacteria and the total quantity of bacteria on surface. The direct control of the quantity of applied bacteria allows the indirect control of the quantity of targeted bacteria, thus constrains the pathogen load on the surface.

While antimicrobial techniques or products represent a broad market, the potential of bacterial products for hygiene is increasingly recognized. Subtractive and additive hygiene both attempt to reduce or inhibit targeted bacteria on the surface.

Subtractive hygiene has the following advantage: The effect on the microflora is quantitative and qualitative since the number as well as the type of the reduced or inhibited microbes, comprising bacteria and viruses, can be influenced. However, this approach has the following disadvantage: The re-colonization of targeted bacteria on the surface between the successive application of antimicrobial techniques or products can only slightly be influenced. Generally, the used antimicrobial techniques or products may not take the risk of bacterial resistance to biocides, and potential cross-resistance to antibiotics, into consideration.

Additive hygiene has the following advantage: The applied bacteria on the surface permanently prevent the colonization of targeted bacteria. However, this approach has the following disadvantage: The effect on the microflora is mostly quantitative since the type of the reduced or inhibited bacteria can only slightly be influenced. Generally, the used bacterial products may not take the human microbiota, especially the skin flora, into consideration.

It is desirable to control the microflora, comprising bacteria and viruses, both quantitative and qualitative. Further, it is desirable to permanently prevent the colonization of targeted bacteria on the surface. The present disclosure addresses the aforementioned deficiencies of additive versus subtractive hygiene and advantageously fills these and other needs for improved hygiene, in particular for the control of targeted microbes on the surface.

SUMMARY

The term "principle of hybrid hygiene" is defined as the iterative application of bacterial products between the successive use of antimicrobial techniques or products through the integration of the cycle of additive hygiene, referred to as additive cycle, in the cycle of subtractive hygiene, referred to as subtractive cycle.

The term "precision hygiene" is defined as data-driven hygiene measure comprising the prescription of bacteria quantity on surface using the right product, at the right rate, in the right place, at the right time.

The term "4R hygiene stewardship" is defined as management principles for precision hygiene. First principle: For each additive cycle (right time), a location-specific (right place) decision about the application rate (right rate) is made. Second principle: For each subtractive cycle (right time), a site-specific (right place) decision about the bacterial product (right product) is made.

The term "precision hygiene strategy" is defined as a machine-learned hygiene strategy for precision hygiene operating with respect to temporal and spatial variability of bacterial exposure on surface by deploying 4R hygiene stewardship.

The term "image-guided hygiene" is defined as procedures for location-specific variable rate application of bacterial products in additive cycles by using head-mounted displays, for example, in combination with a sprayer.

The term "automated precision hygiene" is defined as automation of precision hygiene by using unmanned aerial vehicles for implementing the principle of hybrid hygiene. For example, the transportation industry may benefit from increased flexibility and frequency of hygiene by using prescription drones for antimicrobial or bacterial products.

Embodiments of the subject matter described in the present disclosure are based on the principle of hybrid hygiene and used for the hygienic control of targeted microbes on the surface. Particular embodiments of the subject matter operate with respect to temporal and spatial variability of bacterial exposure on the surface by deploying 4R hygiene stewardship. In some embodiments, a precision hygiene strategy may be implemented using image-guided hygiene or automated precision hygiene.

The disclosure provides methods, systems, and apparatus, including computer programs encoded on computer storage media, for precision hygiene using reinforcement learning. The details of various embodiments of the subject matter of the present disclosure are set forth in the accompanying drawings and the description below. Other features, aspects, and advantages of the subject matter will become apparent from the description, the drawings, and the claims.

DETAILED DESCRIPTION

The disclosure is not limited to the illustrative embodiments described in the following detailed description in which reference is made to the accompanying figures. Modifications and alternative embodiments will be apparent to the skilled person, all of which are explicitly contemplated herein.

Domain-Specific Framework

Figure 1:
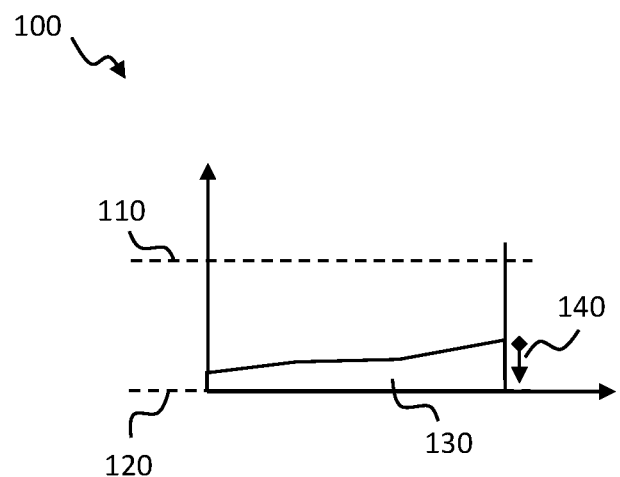
FIG. 1 shows the working approach of subtractive hygiene.

FIG. 1 shows the working approach 100 of subtractive hygiene. The axis of abscissae corresponds to time and the axis of ordinates represents bacteria quantity on bounded surface. An upper threshold 110 constitutes the maximum of the bacteria quantity on bounded surface. The use of antimicrobial techniques or products facilitates a direct control 140 of the quantity of targeted bacteria 130. Subtractive hygiene aims to reduce the quantity of the targeted bacteria 130 towards a lower threshold 120 through antibacterial effects.

Figure 2:
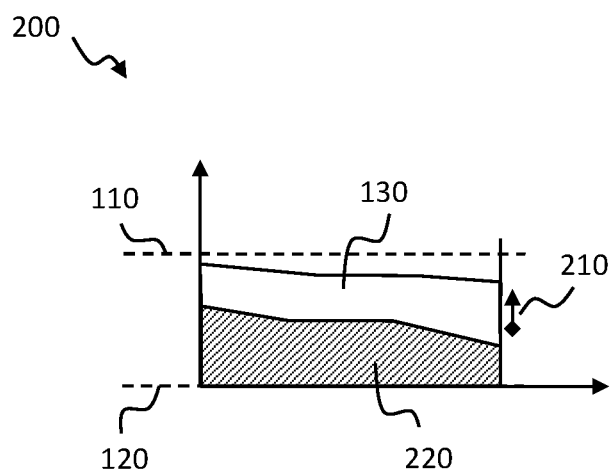
FIG. 2 shows the working approach of additive hygiene.

FIG. 2 shows the working approach 200 of additive hygiene. The axis of abscissae corresponds to time and the axis of ordinates represents bacteria quantity on bounded surface. The upper threshold 110 constitutes the maximum of the bacteria quantity on bounded surface. The application of bacterial products facilitates an indirect control 210 of the quantity of the targeted bacteria 130. Additive hygiene aims to reduce the quantity of the targeted bacteria 130 towards the upper threshold 110 through competition with applied bacteria 220 from the bacterial product.

Figure 3:
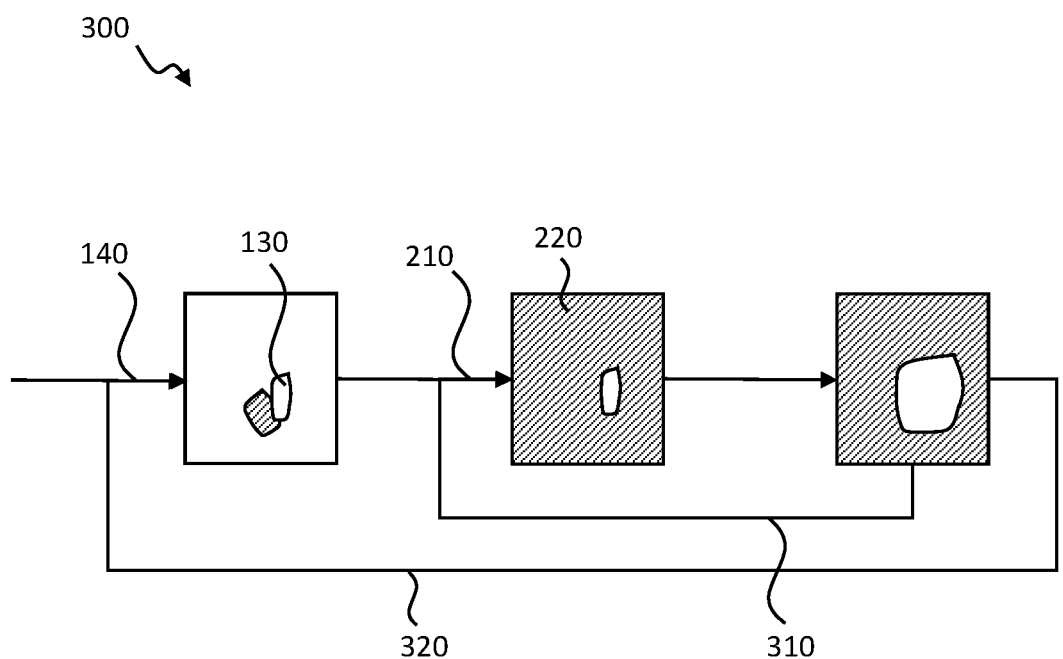
FIG. 3 shows the working approach of the principle of hybrid hygiene.

FIG. 3 shows the working approach 300 of the principle of hybrid hygiene. The iterative application of bacterial products is integrated into the repeated use of antimicrobial techniques or products. The use of antimicrobial techniques or products facilitates the direct control 140 and the application of bacterial products facilitates the indirect control 210 of the quantity of the targeted bacteria 130. The principle of hybrid hygiene aims to reduce the quantity of the targeted bacteria 130 through competition with the applied bacteria 220 from the bacterial product in additive cycles 310 and through antibacterial effects in subtractive cycles 320.

Reinforcement Learning Framework

Generally, a reinforcement learning system selects actions to be performed by an agent that interacts with an environment by receiving observations, in response, performing actions from a set of actions. The agent then receives next observations in response to the actions being performed. The goal of the agent is to learn selecting actions as to maximize some form of cumulative reward. In open-loop mode, the reinforcement learning system may select actions to be performed by the agent without receiving observations.

A real-world system with partial observability, in which the observation does not fully characterize the state of the environment, may be converted into a fully observable environment. An approach may be temporal integration in the observation, for example, by incorporating a plurality of temporal distributed data, or temporal integration in the state representation by incorporating history as sequence of observations and actions. Another approach may be the use of recurrent neural networks that input the current observation to construct an internal state of the environment.

A Markov decision process M=(S, A, T, R) may be discrete- or continuous-time and describes the environment for reinforcement learning comprising a state space S, an action space A, a transition function T, and a reward function R. The state and action space may be low or high dimensional, wherein each dimension may be discrete or continuous. The transition function may be deterministic or probabilistic. The reward function may further be scalar- or vector valued, wherein each value may correspond to an objective.

It is often assumed that the state and action space are known, while the dynamics model is unknown. Under this assumption, a model of the environment comprises a parametrized representation of the transition dynamics. In model-based reinforcement learning, the agent learns a model from experience through iterative updates and plans a policy, explicit or implicit via value function, from the model. In model-free reinforcement learning, the agent learns a policy, explicit or implicit, from experience through iterative updates (policy-based, value-based, or actor-critic approach). In integrated architectures of reinforcement learning, the agent learns both a model and a policy from experience.

Functional Translation

Observation. In embodiments, an observation comprises data from the mapping of applied bacteria. In some embodiments, the observation comprises additional data, for example, about surface properties or environmental conditions. In some embodiments, the observation comprises a plurality of temporal distributed data, for example, a data stream. In some embodiments, the agent receives the observation signal from one or more physical entities, the physical entities comprising mapping tools, wherein the mapping tools comprise any manual, semi-autonomous, or autonomous devices configured to be used for the mapping of applied bacteria. In some embodiments, the observation signal comprises a plurality of temporal distributed signals.

Action. In embodiments, an action comprises data for the prescription of a bacterial product. In some embodiments, the action comprises additional data, for example, for the adjustment of environmental conditions. In some embodiments, the agent sends the action signal to one or more physical entities, the physical entities comprising prescription tools, wherein the prescription tools comprise any manual, semi-autonomous, or autonomous devices configured to be used for the prescription of the bacterial product.

Structural Translation

Actor. Application rates may be selected. Translated, this means that the reinforcement learning system comprises one or more actors, wherein each actor executes on a respective computing unit, wherein each actor is configured to perform operations for selecting actions.

Learner. Selecting the application rates may be learned. Translated, this means that the reinforcement learning system further comprises one or more learners, wherein each learner executes on a respective computing unit, wherein each learner is configured to perform operations for learning a strategy for selecting actions.

P-actor. Bacterial products may be selected. Translated, this means that the reinforcement learning system further comprises zero or more p-actors, wherein each p-actor executes on a respective computing unit, wherein each p-actor is configured to perform operations for selecting contexts.

P-learner. Selecting the bacterial products may be learned. Translated, this means that the reinforcement learning system further comprises zero or more p-learners, wherein each p-learner executes on a respective computing unit, wherein each p-learner is configured to perform operations for learning a strategy for selecting contexts.

Systemic Translation

A single reinforcement learning system may be defined to select one or more actions, wherein the reinforcement learning system comprises one or more actors, one or more learners, zero or more p-actors, and zero or more p-learners. This is solely a matter of formalism, other translations are feasible, for example, defining multiple reinforcement learning systems, wherein each reinforcement learning system may have a correspondence to elements of the set of the one or more actors, one or more learners, zero or more p-actors, and zero or more p-learners.

A single agent may be defined to perform the one or more actions selected by the single reinforcement learning system. This is solely a matter of formalism, other translations are feasible, for example, defining multiple agents, wherein each agent may have a correspondence to elements of the set of the one or more actors.

A single environment may be defined to be interacted with by the single agent to perform the one or more actions selected by the single reinforcement learning system. This is solely a matter of formalism, other translations are feasible, for example, defining multiple environments, wherein each environment may have a correspondence to elements of the set of the single or multiple agents, and single or multiple reinforcement learning systems.

Conceptual Translation

Temporal variability. The application rates may be selected for each additive cycle, and the bacterial products may be selected for each subtractive cycle. Translated, this means that each actor is configured to operate repeatedly, and each p-actor is configured to operate periodically, wherein the frequency of operating repeatedly is higher than the frequency of operating periodically.

Spatial variability. The application rates may be location-specific selected, and the bacterial products may be site-specific selected. Translated, this means that each actor is configured to operate on a surface part y, and each p-actor is configured to operate on a surface class [y], wherein the surface class comprises one or more surface parts.

Learning efficiency. Selecting the application rates may be site-specific learned, and selecting the bacterial products may be institution-specific learned. Translated, this means that each learner is configured to operate on a surface class [y], and each p-learner is configured to operate on a surface group Y, wherein the surface group comprises one or more surface classes.

Algorithmic Translation

Non-stationarity. The data from the mapping of applied bacteria on a surface part may indicate temporary stationary growth behavior. Translated, this means that a transition function may depend on a context p. In some embodiments, the transition function may be defined as $T_p$, wherein the context corresponds to a product mode.

Risk assessment. The data from the mapping of applied bacteria on a surface part may indicate potentially risky growth behavior. Translated, this means that a reward function may depend on a surface class [y]. In some embodiments, the reward function may be defined as $R_{[y]}$, wherein the surface class corresponds to a risk potential.

Multiple tasks. The data from the mapping of applied bacteria on a surface part may indicate task-specific growth behavior. Translated, this means that a task may depend on a context p and surface class [y]. In some embodiments, the task environment may be defined as $M_p^{[y]}=(S, A, T_p, R_{[y]})$ representing a Markov decision process with state space $S$, action space $A$, transition function $T_p$, and reward function $R_{[y]}$.

Uncertainty. The data from the mapping of applied bacteria on a surface part may indicate nondeterministic growth behavior. Translated, this means that a transition function may be probabilistic. In some embodiments, the transition probability may be defined as the context-dependent probability of transition to state s' after selecting action a in state s given by $T_p(s,a,s')=\mathbb{P}_p(s'|s,a)$, wherein state, action, and successor state represent values of random variables respectively. In some embodiments, the expected reward may be defined as the surface-class- and context-dependent expected value of the random variable for the reward after selecting action a in state s given by $R_{[y],p}(s,a)=\mathbb{E}_{[y],p}(R|s,a)$, wherein state and action represent values of random variables respectively. The reduced reward function $R_{[y],p}$ is based on the transition function $T_p$ and the reward function $R_{[y]}$.

Partial observability. The data from the mapping of applied bacteria on a surface part may indicate not fully observable growth behavior. Translated, this means that a policy function may be stochastic. In some embodiments, the action probability may be defined as the surface-class- and context-dependent probability of selecting action a in state s given by $\pi_p^{[y]}(s,a)=\mathbb{P}_p^{[y]}(a|s)$, wherein state and action represent values of random variables respectively. In some embodiments, the policy function may be generalized across contexts and/or surface classes (e.g. meta-learning, multi-task learning, transfer learning). Without generalization, the policy function may be trained to gain reward in the task environment $M_p^{[y]}$. In some embodiments, the policy function may be deterministic, as a special case of stochasticity, and a memory-based approach may be used, for example, through temporal integration in the observation or in the state representation, or by constructing an internal state of the environment using recurrent neural networks.

Large state space. The data from the mapping of applied bacteria on a surface part may indicate environmental complex growth behavior. Translated, this means that a transition or policy function may be generalized across states. In model-free reinforcement learning, the generalization capacity may rely on the inductive bias that actions have similar values in similar states. In some embodiments, the policy function may be parametrized and denoted with $\pi_p^{[y]}{}_\theta$ wherein $\theta$ refers to the parameters of an approximator, for example, the bias and weights of a neural network. The policy function may be learned, explicit or implicit (value-based, policy-based, actor-critic), by iteratively updating the parameters of the function approximator. In some embodiments, a single function approximator may represent multiple policy functions, for example, a plurality of policy functions for different contexts but the same surface class may be represented by the approximator. Exemplary mentioned may be a contextual policy function $\pi^{[y]}{}_\theta$ wherein the input comprises the context. In model-based reinforcement learning, the generalization capacity may rely on the inductive bias that actions have similar effects in similar states. In some embodiments, the transition function may be parametrized and denoted with $T_{p,\theta}$ wherein $\theta$ refers to the parameters of an approximator, for example, the bias and weights of a neural network. The transition function may be learned by iteratively updating the parameters of the function approximator. In some embodiments, a single function approximator may represent multiple transition functions, for example, a plurality of transition functions for different contexts may be represented by the approximator. Exemplary mentioned may be a contextual transition function $T_\theta$ wherein the input comprises the context. In integrated architectures of reinforcement learning, one or more transition and policy functions may be learned.

Domain-Specific Reinforcement Learning

In embodiments, each p-learner is configured to operate on a surface group Y and the strategy for selecting contexts of each p-learner may be denoted with $\mu^Y$. In some embodiments, the strategy for selecting contexts of each p-learner may be generalized across surface groups. In embodiments, each learner is configured to operate on a surface class [y] and the strategy for selecting actions of each learner may be denoted with $\mu^{[y]}$. In some embodiments, the strategy for selecting actions of each learner may be generalized across surface classes.

In embodiments, learning the strategy for selecting actions of each learner comprises learning one or more policy functions, for example, the policy function $\pi_p^{[y]}$ for each context, and/or learning one or more models, for example, the transition function $T_p$ for each context, and planning one or more policy functions. In some embodiments, learning the strategy for selecting actions of each learner may comprise learning a generalized policy function, for example, the policy function $\pi_p^{[y]}$ may be generalized across contexts and/or surface classes (e.g. meta-learning, multi-task learning, transfer learning). In some embodiments, learning the strategy for selecting actions of each learner may comprise learning a generalized transition function, for example, the transition function $T_p$ may be generalized across contexts.

In embodiments, the strategy for selecting actions of each learner may be implemented using reinforcement learning, for example, using policy search, actor-critic, trajectory optimization, model predictive control, or a Monte Carlo approach. In embodiments, the reinforcement learning techniques comprise model-free (value-based, policy-based, actor-critic), model-based, and integrated approaches. In some embodiments, the reinforcement learning techniques may be combined with supervised or imitation learning. In embodiments, the reinforcement learning techniques comprise open-loop, closed-loop, and mixed open-closed-loop control, wherein the strategy for selecting actions of each learner may operate on action-, trajectory-, or task-level. For example, the strategy for selecting actions of each learner may be deployed using open-loop trajectory planning without state feedback based on a model trained on experience data with state feedback. The disclosure therefore naturally comprises control methods in the open-loop mode. In embodiments, each actor may perform operations independently of each other actor in open-loop, closed-loop, or mixed open-closed-loop mode. In some embodiments, actions or observations from actors in closed-loop mode may be inferred to actors in open-loop mode.

In some embodiments, the strategy for selecting contexts of each p-learner may be implemented using reinforcement learning, for example, using a high-level Markov decision process, task sequencing, task scheduling, curriculum learning, or hierarchical learning. In other embodiments, the strategy for selecting contexts of each p-learner may be implemented using any methods other than reinforcement learning, for example, machine learning, optimization, heuristic, or rule-based techniques.

The term "HygieneLearning" is defined as procedures for learning a strategy for selecting actions, wherein the actions are selected to be performed by an agent that interacts with an environment by receiving observations, in response, performing actions from a set of actions, wherein the observations comprise data from the mapping of applied bacteria, and wherein the actions comprise data for the prescription of a bacterial product.

An example procedure for "HygieneLearning" is shown below. The disclosure is not limited to the illustrative embodiment. The reinforcement learning system shown in the procedure comprises one or more actors and one or more learners. In the procedure shown below, contexts may be manually selected. While the architecture follows the principles of temporal and spatial variability, the one or more learners may operate according to any update schema comprising batch, mini-batch, incremental, online, semi-online, offline approaches. The arrangement of the learners should therefore not be construed as limitation on the scope of the present disclosure. The procedure shown below comprises one or more contexts, one or more surface parts, and one or more surface classes, wherein each surface class comprises one or more surface parts. Further, an episode may be generalized and referred to as periodically, while a stage may be generalized and referred to as repeatedly.

HygieneLearning Procedure I

```
DEFINE p, y, [y], e, n
# Context, surface part, surface class, episode, stage
INITIALIZE each μ[y]
FOR each surface class [y] DO
    FOR each episode e DO
        Select context p for training μ[y]
        Train μ[y] based on experience data          # Learner
        FOR each surface part y of surface class [y] DO
            FOR each stage n of episode e DO
                Generate experience data using μ[y]   # Actor
            ENDFOR
        ENDFOR
    ENDFOR
ENDFOR
```

© 2020 Olivia Grabmaier

Another example procedure for "HygieneLearning" is shown below. The disclosure is not limited to the illustrative embodiment. The reinforcement learning system shown in the procedure comprises one or more actors, one or more learners, one or more p-actors, and one or more p-learners. The sequential arrangement of the p-learners, p-actors, learners, and actors as shown in the procedure is by way of example. Furthermore, the nesting of the loops as shown in the procedure is by way of example. While the architecture follows the principles of temporal and spatial variability, the one or more learners and one or more p-learners may operate according to any update schema comprising batch, mini-batch, incremental, online, semi-online, offline approaches. The arrangement of the learners and p-learners should therefore not be construed as limitation on the scope of the present disclosure. The procedure shown below comprises one or more contexts, one or more surface parts, one or more surface classes, and one or more surface groups, wherein each surface group comprises one or more surface classes, and wherein each surface class comprises one or more surface parts. While the real-world system indicates a natural termination condition with the end of each subtractive cycle of finite length, the reinforcement learning system may, in some cases, be defined as infinite horizon problem. While the real-world system indicates a natural discrete-time action execution with each additive cycle of finite length, the reinforcement learning system may, in some cases, be defined as continuous-time Markov decision process. In some embodiments, the strategy for selecting actions of each learner may involve a behavior strategy, wherein the behavior strategy may comprise a trade-off between an action preference, exploitation based on the target strategy, and exploration in the action selection. In some embodiments, the strategy for selecting contexts of each p-learner may involve a behavior strategy, wherein the behavior strategy may comprise a trade-off between a context preference, exploitation based on the target strategy, and exploration in the context selection.

---

HygieneLearning Procedure II

---

DEFINE p, a, y, [y], Y, e, n
Context, action, surface part, surface class, surface group, episode, stage
INITIALIZE each $\mu^Y$, $\mu^{[y]}$
FOR each surface group Y DO
    Learn $\mu^Y$ for selecting contexts               # P-learner
    FOR each surface class [y] of surface group Y DO
        FOR each episode e DO
            Select context p according to $\pi^Y$    # P-actor
            Learn $\mu^{[y]}$ for selecting actions    # Learner
            FOR each surface part y of surface class [y] DO
                FOR each stage n of episode e DO
                      Select action a according to $\mu^{[y]}$    # Actor
                ENDFOR
            ENDFOR
        ENDFOR
    ENDFOR
ENDFOR

---

© 2020 Olivia Grabmaier

Figure 4:
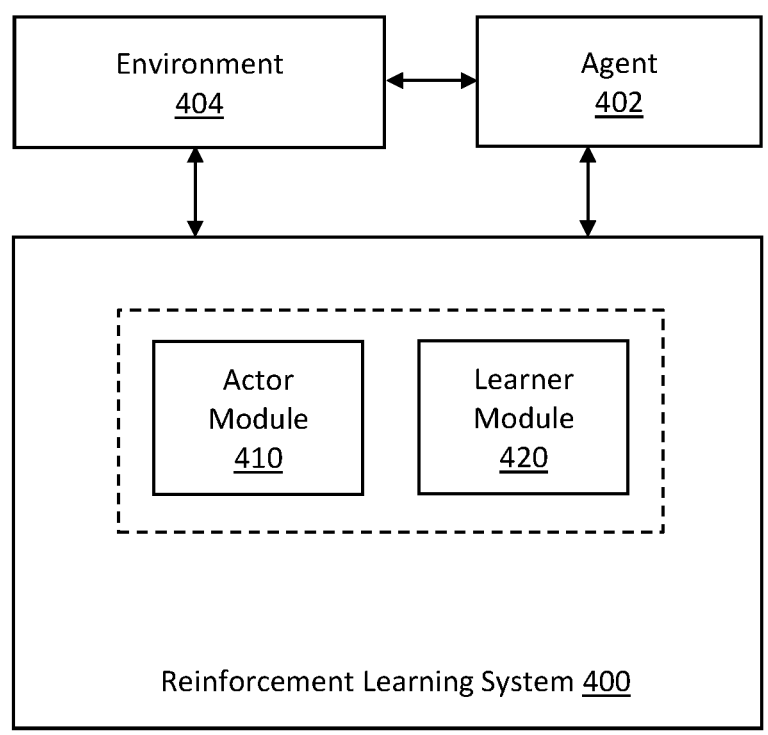
FIG. 4 shows an example reinforcement learning system for training rate.

FIG. 4 shows an example reinforcement learning system 400 for training rate. The reinforcement learning system 400 selects actions to be performed by an agent 402 that interacts with an environment 404 by receiving observations, in response, performing actions from a set of actions. In embodiments, the reinforcement learning system 400 comprises an actor module 410. The actor module 410 comprises one or more actors, wherein each actor executes on a respective computing unit, wherein each actor is configured to operate on a surface part distinct from operations of each other actor, wherein each actor is configured to repeatedly perform operations for selecting an action to be performed by the agent. In some embodiments, one or more of the actors receive an action preference and process, prior to selecting the action, the action preference. In some embodiments, the one or more of the actors receive the action preference signal from one or more physical entities, the physical entities comprising computer-implemented decision support tools, for example, smart devices, IoT devices, or computer devices configured to execute one or more programs with at least one user interface for the action preference input. In embodiments, the reinforcement learning system 400 comprises a learner module 420. The learner module 420 comprises one or more learners, wherein each learner executes on a respective computing unit, wherein each learner is configured to operate on a surface class distinct from operations of each other learner, wherein each learner is configured to perform operations for learning a strategy for selecting actions.

Figure 5:
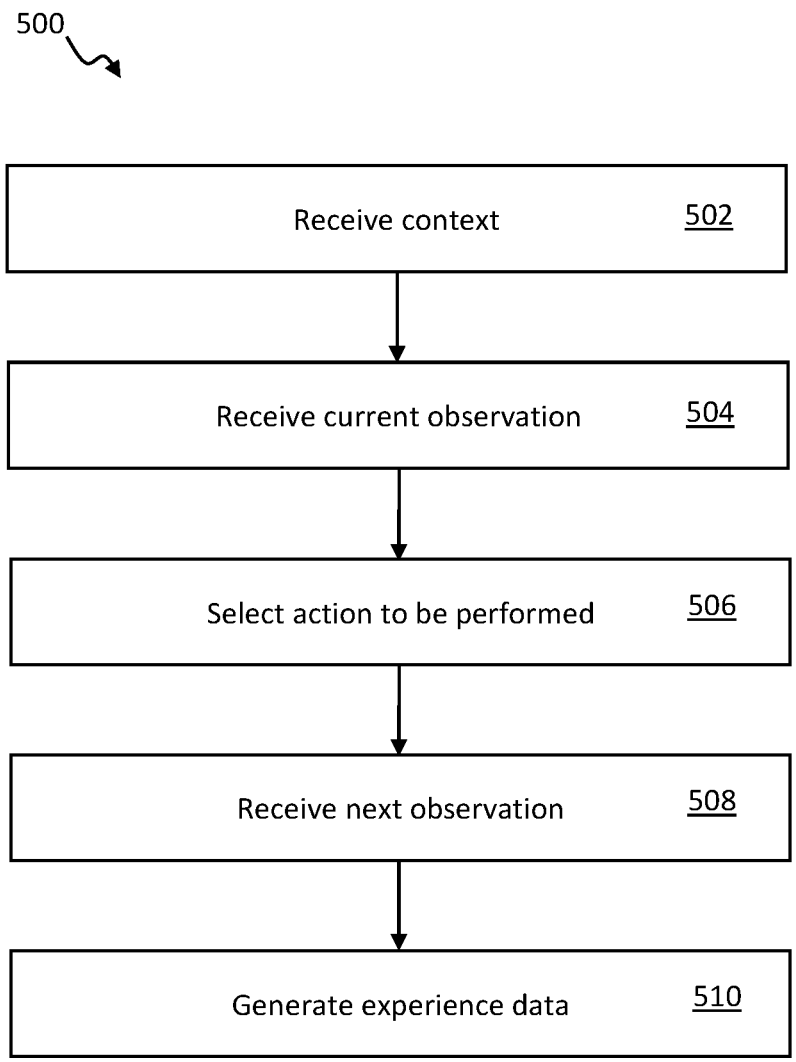
FIG. 5 shows an example process of operations performed by an actor.

FIG. 5 shows an example process 500 of operations that will be described, for convenience, as being performed by an actor of the one or more actors. The actor may perform operations of the process independently of and asynchronously from each other actor. In step 502, the actor receives, periodically, a context, wherein the context comprises a bacterial product to be prescribed on a surface part. In step 504, the actor receives a current observation from the agent interacting with the environment, wherein the observation comprises data from the mapping of applied bacteria on the surface part. In some embodiments, the agent receives the observation signal from one or more physical entities, the physical entities comprising mapping tools, for example, unmanned aerial vehicles, smart devices, IoT devices, robotic devices, configured to be used for the mapping of applied bacteria on the surface part. In step 506, the actor selects an action to be performed by the agent, wherein the action comprises data for the prescription of the bacterial product on the surface part. In some embodiments, the agent sends the action signal to one or more physical entities, the physical entities comprising prescription tools, for example, unmanned aerial vehicles, head-mounted displays, robotic devices, configured to be used for the prescription of the bacterial product on the surface part. In step 508, the actor receives a next observation from the agent interacting with the environment. In step 510, the actor generates experience data comprising the current observation, the selected action, and the next observation. In some embodiments, the experience data further comprises a reward received by the actor in response to the action being performed.

Figure 6:
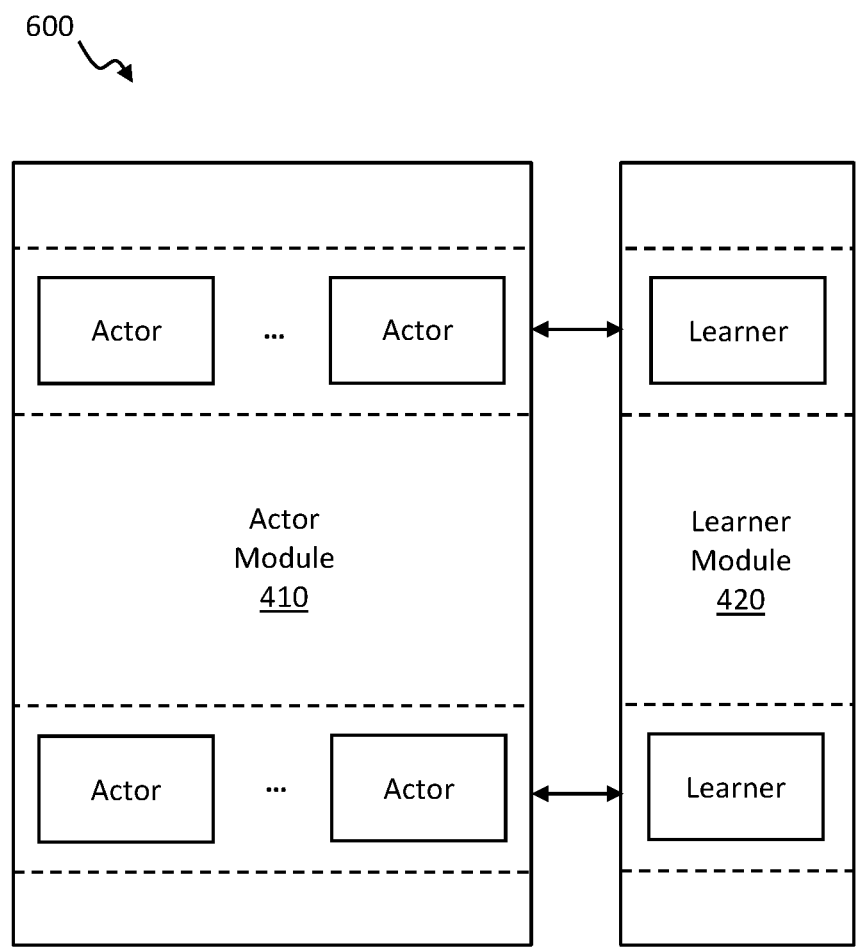
FIG. 6 shows an example interaction between actor and learner module.

FIG. 6 shows an example interaction 600 between the actor and learner module. In embodiments, the reinforcement learning system 400 comprises the actor module 410. Each actor of the actor module 410 is configured to operate on a surface part distinct from operations of each other actor. In embodiments, the reinforcement learning system 400 comprises the learner module 420. Each learner of the learner module 420 is configured to operate on a surface class distinct from operations of each other learner, wherein the surface class comprises one or more surface parts, and wherein each learner interacts with one or more of the actors, wherein each of the one or more of the actors is configured to operate on one of the surface parts of the surface class on which the learner is configured to operate.

Figure 7:
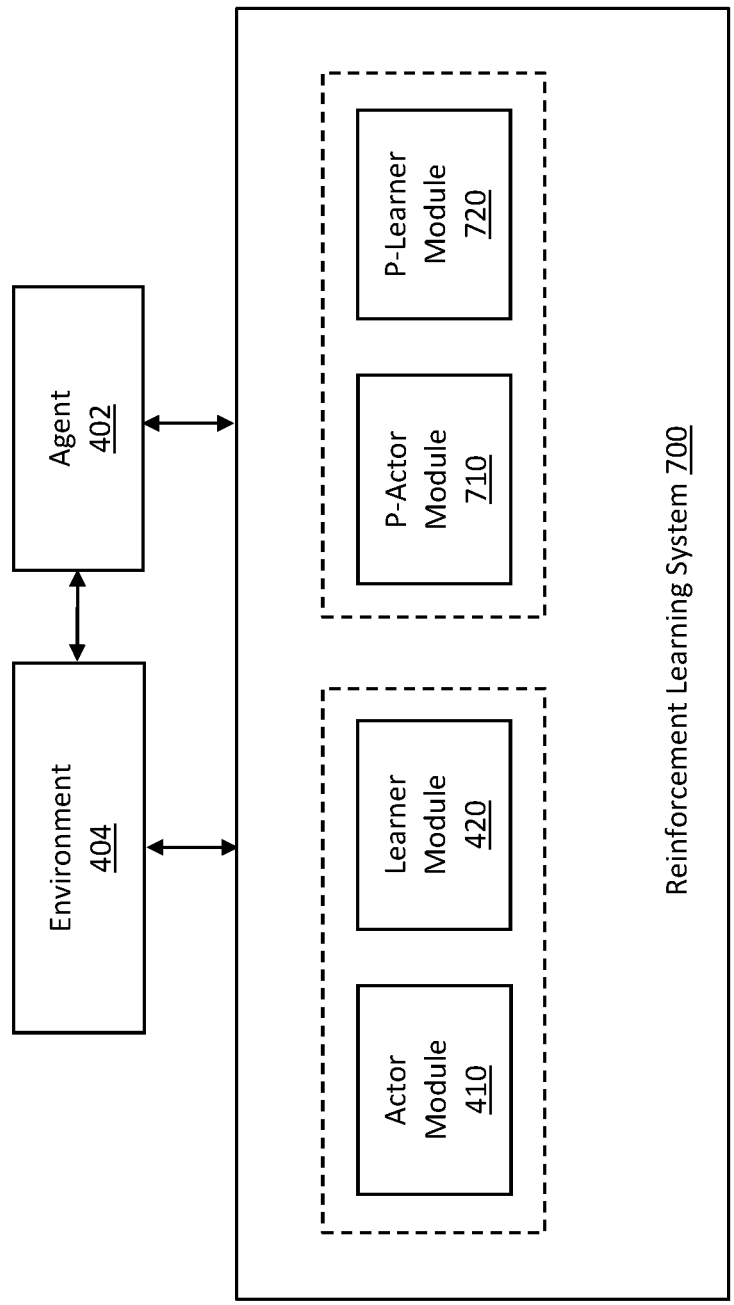
FIG. 7 shows an example reinforcement learning system for training rate and product.

FIG. 7 shows an example reinforcement learning system 700 for training rate and product. The reinforcement learning system 700 selects actions to be performed by the agent 402 that interacts with the environment 404 by receiving observations, in response, performing actions from a set of actions. In embodiments, the reinforcement learning system 700 comprises the actor module 410 and the learner module 420. In embodiments, the reinforcement learning system 700 further comprises a p-actor module 710. The p-actor module 710 comprises one or more p-actors, wherein each p-actor executes on a respective computing unit, wherein each p-actor is configured to operate on a surface class distinct from operations of each other p-actor, wherein each p-actor is configured to periodically perform operations for selecting a context. In some embodiments, one or more of the p-actors receive a context preference and process, prior to selecting the context, the context preference. In some embodiments, the one or more of the p-actors receive the context preference signal from one or more physical entities, the physical entities comprising computer-implemented decision support tools, for example, smart devices, IoT devices, or computer devices configured to execute one or more programs with at least one user interface for the context preference input. In embodiments, the reinforcement learning system 700 further comprises a p-learner module 720. The p-learner module 720 comprises one or more p-learners, wherein each p-learner executes on a respective computing unit, wherein each p-learner is configured to operate on a surface group distinct from operations of each other p-learner, wherein each p-learner is configured to perform operations for learning a strategy for selecting contexts.

Figure 8:
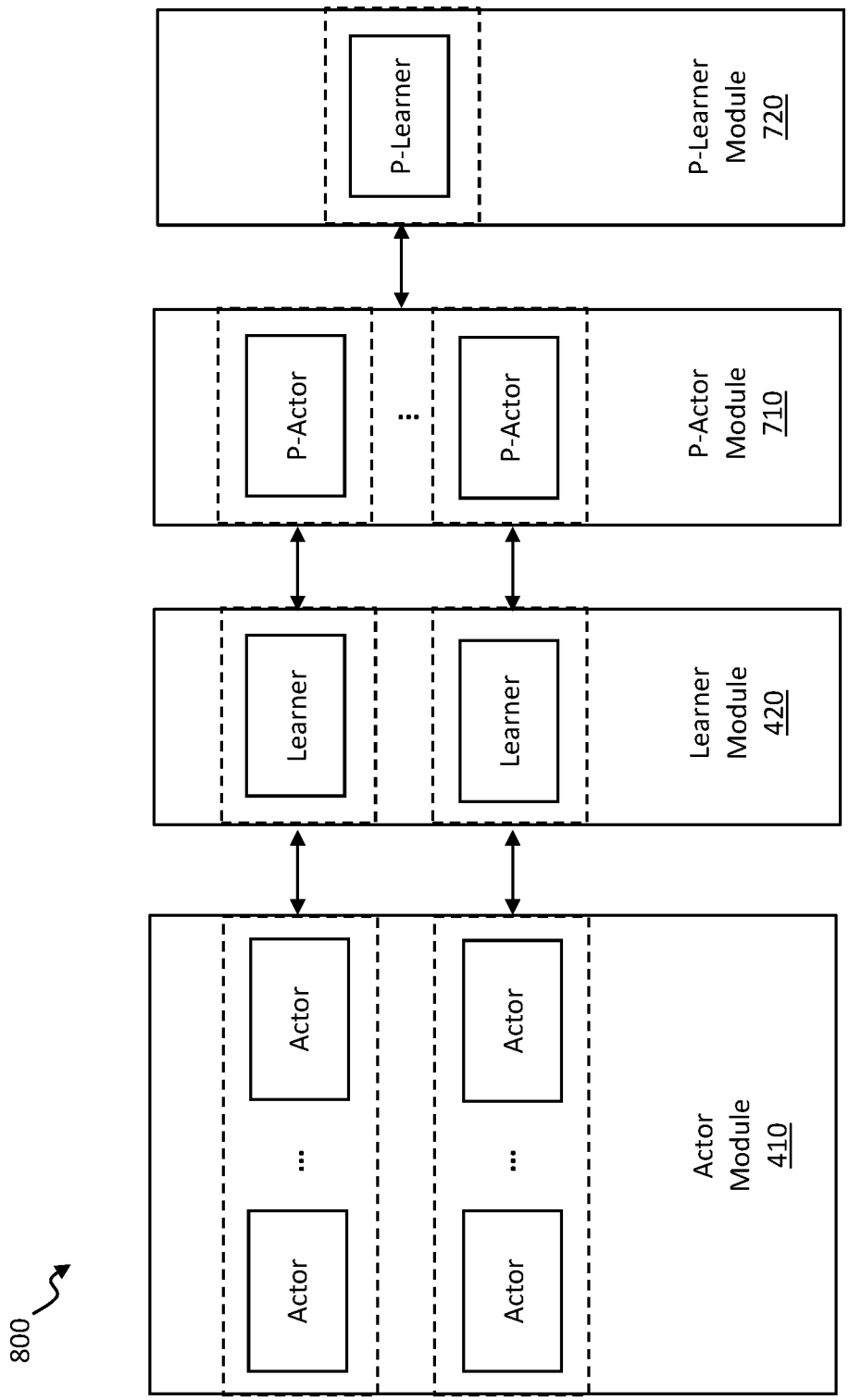
FIG. 8 shows an example interaction between actor, learner, p-actor, and p-learner module.

FIG. 8 shows an example interaction 800 between the actor, learner, p-actor, and p-learner module. In embodiments, the reinforcement learning system 700 comprises the actor module 410. Each actor of the actor module 410 is configured to operate on a surface part distinct from operations of each other actor. In embodiments, the reinforcement learning system 700 comprises the learner module 420. Each learner of the learner module 420 is configured to operate on a surface class distinct from operations of each other learner, wherein the surface class comprises one or more surface parts, and wherein each learner interacts with one or more of the actors, wherein each of the one or more of the actors is configured to operate on one of the surface parts of the surface class on which the learner is configured to operate. In embodiments, the reinforcement learning system 700 further comprises the p-actor module 710. Each p-actor of the p-actor module 710 is configured to operate on a surface class distinct from operations of each other p-actor, wherein each p-actor may interact with one of the learners, wherein the one of the learners is configured to operate on the surface class on which the p-actor is configured to operate. In embodiments, the reinforcement learning system 700 further comprises the p-learner module 720. Each p-learner of the p-learner module 720 is configured to operate on a surface group distinct from operations of each other p-learner, wherein the surface group comprises one or more surface classes, wherein each p-learner interacts with one or more of the p-actors, wherein each of the one or more of the p-actors is configured to operate on one of the surface classes of the surface group on which the p-learner is configured to operate.

Ethics

The following ethics section serves the sufficiency of disclosure and aims the responsible use of AI systems by providing further details on how some embodiments of the subject matter described in the present disclosure may be practiced. A transparent documentation throughout development, deployment, and maintenance ensures confidence in AI services for large-scale applications. The design of AI-based systems for precision hygiene demands regulatory compliance and ethical alignment. The ethical principles for deploying the HygieneLearning procedures preferably include safety, privacy, and human agency. In some embodiments, the principle of safety may be accomplished by defining performance criteria for hygiene strategies, while ensuring safe and continual improvement. In some embodiments, the principle of human agency may be accomplished by integrating external preferences of the hygiene staff. In some embodiments, the principle of privacy may be accomplished by learning hygiene strategies federatively.

Data related to infection and hygiene management may be privacy sensitive and not shared in some fields of application. Exemplary mentioned may be the healthcare industry that is involved in the intranational spread of antimicrobial resistant (AMR) bacteria and the transportation industry that is further involved in the international spread. Healthcare- and transportation-associated infections represent a serious threat to public health with increased human mortality and morbidity. In some fields of application, for example, healthcare institutions, e.g. hospitals, and transportation institutions, e.g. airports, there is a need for improved hygiene while preserving privacy.

In some embodiments, the HygieneLearning procedures may be deployed in a federated learning setting, wherein the data is distributed over multiple devices, and wherein hygiene strategies may be updated on-device. The federated reinforcement learning system may be deployed using centralized, decentralized, or distributed communication architectures. In some embodiments, a peer-to-peer or server-client architecture may be used. The federated reinforcement learning system may be deployed using linear or non-linear representations. In some embodiments, neural networks may be used as function approximators. It will be apparent to the skilled person that the use of privacy-preserving mechanisms does not limit the scope of the disclosure and should be considered as an optional, claimed method for deploying the HygieneLearning procedures. Alternative methods for the deployment will be apparent to the skilled person.

The term "Federated HygieneLearning" is defined as procedures for federated learning a global strategy for selecting actions, wherein the actions comprise data for the prescription of a bacterial product, wherein the global strategy is updated each round by a plurality of federated learners that receive the global strategy from a federator, in response, determine and send one or more local updates to the federator, wherein each local update is based at least in part on a subset of local experience data.

In some embodiments, the global strategy is a neural network that is configured to receive an input comprising an observation, wherein the observation comprises data from the mapping of applied bacteria, and to generate a neural network output from the input in accordance with a set of parameters, wherein federated learning the global strategy comprises updating the values of the set of parameters of the neural network. In some embodiments, the input received by the neural network further comprises an action, wherein the action comprises data for the prescription of a bacterial product. In some embodiments, the input received by the neural network further comprises a context, wherein the context comprises the bacterial product to be prescribed. In some embodiments, updating the values of the set of parameters of the neural network comprises determining, by each federated learner, a local update to the global strategy based at least in part on a gradient vector, wherein the gradient vector is determined by performing one or more iterations of one or more gradient training techniques on the global strategy with respect to local experience data. In some embodiments, the one or more iterations of the one or more gradient training techniques may be performed with respect to one or more data batches of the local experience data. In some embodiments, the one or more iterations of the one or more gradient training techniques may be performed with respect to one or more data examples of the local experience data. The gradient training techniques comprise gradient ascent (e.g. for policy-based approaches) or descent (e.g. for value-based approaches) techniques, for example, batch gradient techniques or stochastic gradient techniques.

An example procedure for "Federated HygieneLearning" is shown below. The disclosure is not limited to the illustrative embodiment. The federated reinforcement learning system shown in the procedure comprises one or more federators and one or more federated learners. The sequential arrangement of the federators and federated learners as shown in the procedure is by way of example. Further, the procedure shown below comprises one or more local surface classes and one or more global surface classes, wherein each global surface class comprises one or more local surface classes, and wherein each local surface class comprises one or more surface parts. Each federator of the one or more federators communicates each round with a plurality of federated learners for federated learning a global strategy for selecting actions, wherein the plurality of federated learners consists of one or more federated learners and may vary in different rounds. In a round in which the plurality of federated learners consists of a single federated learner, the global update may be determined by aggregating a single local update. In some embodiments, each federated learner may satisfy an eligibility criterion prior to participating in a round. In some embodiments, each federated learner may be selected for the participation in the round depending on the local version of the global strategy. In some embodiments, rounds may be ordered in a temporal sequence. In some embodiments, rounds may indicate a temporal overlap. It will be apparent to the skilled person that the procedure shows an isolated round without temporal relation to other rounds. The procedure comprises asynchronous, wherein the global update is determined through asynchronous aggregation of local updates, and synchronous, wherein the global update is determined through synchronous aggregation of local updates, techniques for federated learning a global strategy for selecting actions.

---

Federated HygieneLearning Procedure

---

DEFINE k, $[y]_k$, $[y]$, $\mu^{[y]}_{\theta_j}$, $\theta_j$
    # local index, local surface class, global surface class,
    global strategy, global parameter
INITIALIZE $\theta_0$ for each $\mu^{[y]}_{\theta_j}$
FOR round j DO
    FOR local surface class $[y]_k$ of global    # Federated learner
    surface class [y] DO
        Receive global strategy $\mu^{[y]}_{\theta_j}$
        Determine local update $\theta_j \leftarrow$ LocalAggregate{ }
        Send local update $(\theta_j, k)$
    ENDFOR
    FOR global surface class [y] DO    # Federator
        Receive local updates $(\theta_j, k)$
        Determine global update $\theta_{j+1} \leftarrow$ GlobalAggregate{ }
        Send global strategy $\mu^{[y]}_{\theta_{j+1}}$
    ENDFOR
ENDFOR © 2020 Olivia Grabmaier

---

Figure 9:
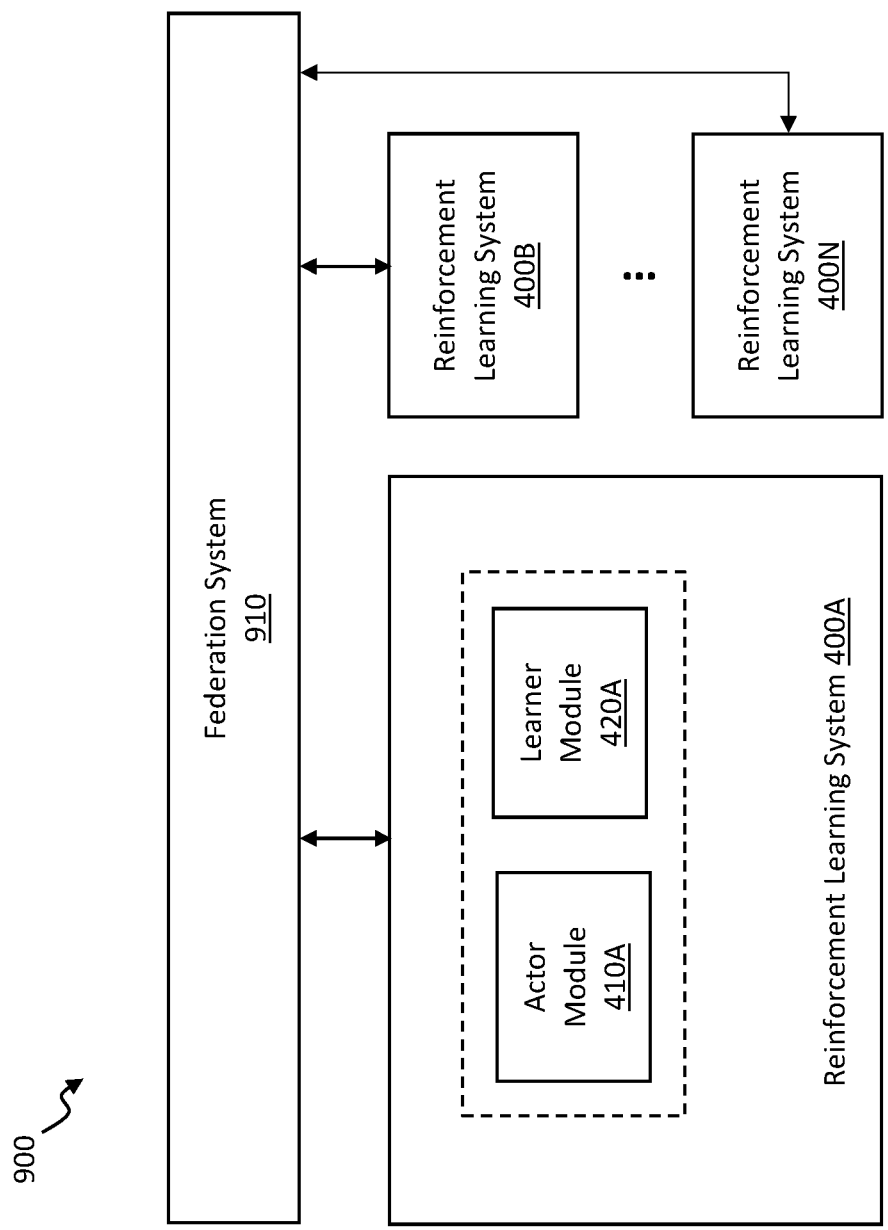
FIG. 9 shows an example federated reinforcement learning system for training rate.

FIG. 9 shows an example federated reinforcement learning system 900 for training rate. In embodiments, the federated reinforcement learning system 900 comprises a federation system 910. The federation system 910 comprises one or more federators, wherein each federator executes on a respective computing unit, wherein each federator is configured to operate on a global surface class distinct from operations of each other federator. In embodiments, the federated reinforcement learning system 900 comprises one or more reinforcement learning systems 400A-400N. Each of the reinforcement learning systems 400A-N may operate independently of and asynchronously from each other reinforcement learning system. Each of the reinforcement learning systems 400A-N comprises an actor module 410A-N and a learner module 420A-N, e.g. the reinforcement learning system 400A comprises the actor module 410A and the learner module 420A. Each of the learner modules 420A-N comprises one or more learners, wherein each learner in the federated reinforcement learning system may be referred to as a federated learner, wherein each federated learner executes on a respective computing unit, wherein each federated learner is configured to operate on a local surface class distinct from operations of each other federated learner. In embodiments, the federation system 910 and the one or more reinforcement learning systems 400A-N may be interconnected by any form or medium of communication, for example, one or more communication networks. In some embodiments, a reinforcement learning system of the reinforcement learning systems 400A-N may be interpreted as a client, for example, a healthcare or transportation institution, and the federation system 910 may be interpreted as one or more servers, for example, edge- or cloud-based servers. In some embodiments, one or more of the reinforcement learning systems 400A-N further comprise a p-actor-module and a p-learner module, such as the reinforcement learning system 700 shown in FIG. 7, and the federated reinforcement learning system 900 may be configured for training rate and product.

Figure 10:
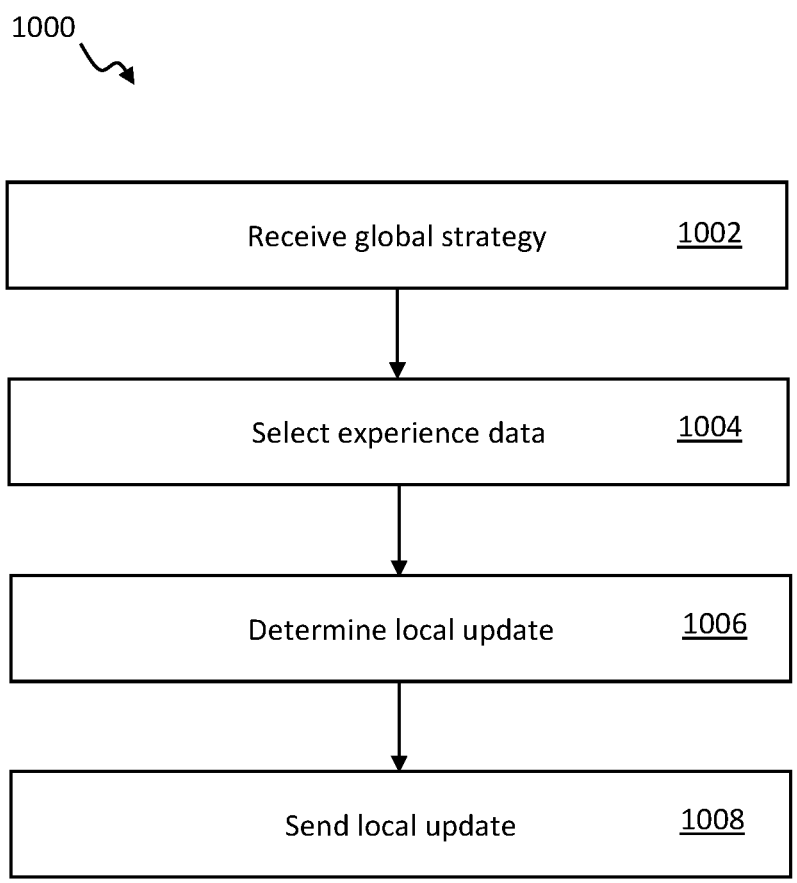
FIG. 10 shows an example process of operations performed by a federated learner.

FIG. 10 shows an example process 1000 of operations that will be described, for convenience, as being performed by a federated learner of the one or more federated learners. The federated learner may perform operations of the process independently of and asynchronously from each other federated learner. In step 1002, the federated learner receives a global strategy from a federator, wherein the federated learner is configured to operate on a local surface class of the global surface class on which the federator is configured to operate. In step 1004, the federated learner selects a subset of local experience data generated by respective actors. In step 1006, the federated learner determines a local update to the global strategy, wherein the local update is based at least in part on the subset of local experience data, and wherein determining, by the federated learner, the local update comprises performing one or more iterations for aggregating the subset of local experience data. In step 1008, the federated learner sends the local update to the federator.

Figure 11:
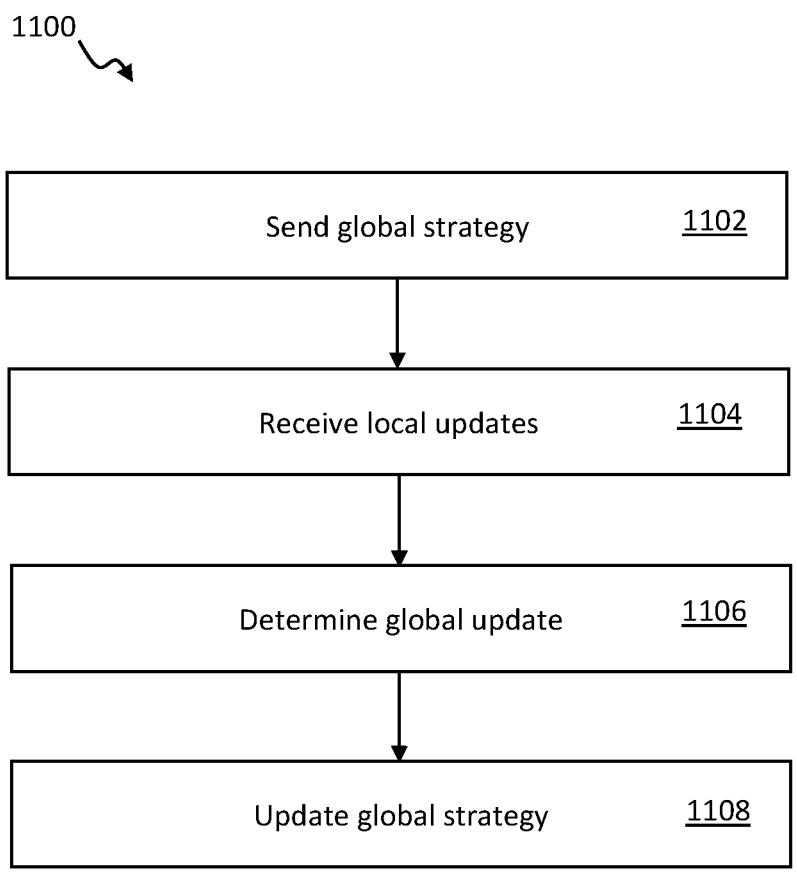
FIG. 11 shows an example process of operations performed by a federator.

FIG. 11 shows an example process 1100 of operations that will be described, for convenience, as being performed by a federator of the one or more federators. The federator may perform operations of the process independently of and asynchronously from each other federator. In step 1102, the federator sends the global strategy to a plurality of federated learners, wherein each federated learner is configured to operate on a local surface class of the global surface class on which the federator is configured to operate. In step 1104, the federator receives one or more local updates from the plurality of federated learners. In step 1106, the federator determines a global update to the global strategy, wherein the global update is based at least in part on a subset of the one or more local updates, and wherein determining, by the federator, the global update comprises performing one or more iterations for aggregating the subset of the one or more local updates. In step 1108, the federator updates the global strategy. In some embodiments, the federator sends the updated global strategy to one or more of the plurality of federated learners.

| HygieneLearning | | | |
|---|---|---|---|
| State space | S | Surface part | y |
| Action space | A | Surface class | [y] |
| Transition function | $T_p$ | Surface group | Y |
| Reward function | $R_{[y]}$ | Stage | n |
| Environment | $M_p^{[y]}$ | Episode | e |
| Strategy for selecting actions | $\mu^{[y]}$ | Action | a |
| Strategy for selecting contexts | $\mu^Y$ | Context | p |
| Federated HygieneLearning | | | |
| Local index | k | Global parameter | $\theta_j$ |
| Local update | $(\theta_j, k)$ | Global strategy | $\mu^{[y]}{}_{\theta_j}$ |
| Local surface class | $[y]_k$ | Local aggregation | LocalAggregate{ } |
| Global surface class | [y] | Global aggregation | GlobalAggregate{ } |

Interpretation

Embodiments of the subject matter described in the present disclosure are based on the principle of hybrid hygiene and used for the hygienic control of targeted microbes on the surface. Particular embodiments of the subject matter operate with respect to temporal and spatial variability of bacterial exposure on the surface by deploying 4R hygiene stewardship. The various embodiments of the subject matter described in the present disclosure illustrate the promise of precision hygiene as data-driven hygiene measure comprising the prescription of bacteria quantity on surface using the right product, at the right rate, in the right place, at the right time. In some embodiments, a predictive approach may be used, wherein the decision making is based on hygiene data that is static during the actual subtractive cycle. In some embodiments, a control approach may be used, wherein the decision making is based on hygiene data that is regularly updated during the actual subtractive cycle.

In embodiments, observations may be interpreted as characteristics data, wherein the observations comprise data from the mapping of applied bacteria. The mapping comprises zero or more tracking technologies, e.g. optical markers, and one or more sensor technologies, e.g. optical sensors. For example, characteristics data may be acquired through sampling, e.g. manual measurements, remote sensing, e.g. IoT devices, or aerial remote sensing, e.g. drones attaching to the surface during mapping. In embodiments, actions may be interpreted as application data, wherein the actions comprise data for the prescription of a bacterial product. The prescription comprises zero or more spraying technologies, e.g. for a liquid bacterial product, and zero or more positioning technologies.

The goal of precision hygiene is to optimize hygiene input on hygiene output by using variable rate technology, wherein the hygiene input comprises one or more bacterial products. In some embodiments, a precision hygiene strategy may be deployed using a map-based approach for variable rate application of hygiene input, wherein the application data for applying hygiene input may be generated as function of the location data based upon one or more prescription maps that correlate application data with location data. In some embodiments, a precision hygiene strategy may be deployed using a sensor-based approach for variable rate application of hygiene input, wherein the application data for applying hygiene input may be generated as direct function of the characteristics data.

EXAMPLE

In embodiments, each surface class comprises one or more surface parts. Due to the different infectiousness and contact frequency, a location-specific infection factor $I_y \in (0,1]$ and transmission factor $T_y \in (0,1]$ may be assigned to each surface part y.

Each surface class may be defined as equivalence class and denoted with [y], whereby y indicates a representative surface part contained in the class. Surface parts y and η may be equivalent if the products of their transmission and infection factor are approximately equal $$y \sim \eta :\Leftrightarrow T_y \cdot I_y \approx T_\eta \cdot I_\eta.$$

The equivalence relation may be applied on an index set of surface parts N, wherein the respective surface group may be defined as quotient set Y=N/~ comprising one or more surface classes [y]∈Y.

For deploying the Federated HygieneLearning procedures, a global index set of surface parts N may be defined, wherein the respective global surface group comprises one or more global surface classes [y], wherein the global index set of surface parts comprises one or more local index sets of surface parts $N_x \subset N$, and wherein each respective local surface group comprises one or more local surface classes $[y]_k$. As an eligibility criterion, a federated learner may be eligible to participate in a round for federated learning a global strategy $\mu^{[y]}{}_{\theta_j}$ if the federated learner is configured to operate on a local surface class $[y]_k \subset [y]$.

The Pathogen Risk Index (PRI) is the location-specific and time-dependent measure for the risk of pathogen transmission given by $$PRI(y, t) = T_y \cdot I_y \cdot [M_{max} - m_y(t)],$$

wherein the mapped quantity of applied bacteria per unit surface may be denoted with $m_y(t)$ and the maximum of bacteria quantity per unit surface may be denoted with $M_{max}$. The index is defined as the probability of the maximum loss, given by the transmission factor, multiplied with the magnitude.

The definition of the Pathogen Risk Index depends on the product of the transmission and infection factor, thus on the surface class. In some embodiments, surface classes may be defined for low-, mid-, and high-risk potential. The reduced reward function is the expected reward given by $$R_{[y],p}(s, a) = \mathbb{E}_{[y],p}(R|s,a) = \int_{s' \in S} T_p(s, a, s') \cdot R_{[y]}(s, a, s')$$

with the reward function $R_{[y]}$. The state, action, and successor state are values of random variables for surface parts y∈[y] respectively. The reward function depends on the surface class, since rewards are assigned with the objective of decreasing the pathogen risk to protect the environment, wherein the Pathogen Risk Index serves as a measure. Optionally, the objective may further comprise increasing the bacteria response to the bacterial product to save resources.

Hardware

The subject matter of the present disclosure provides a system comprising one or more computers and one or more storage devices storing instructions that, when executed by the one or more computers, cause the one or more computers to perform operations for selecting actions to be performed by an agent that interacts with an environment by receiving observations, in response, performing actions from a set of actions, wherein the observations comprise data from the mapping of applied bacteria, and wherein the actions comprise data for the prescription of a bacterial product. The system may comprise one or more processors configured to perform operations for reinforcement learning. An exemplary embodiment may be a digital signal processor (DSP); a central processing unit (CPU) used, for example, within a computer system; a graphics processing unit (GPU) used, for example, for parallelization across multiple processors; a special purpose logic circuitry used, for example, for hardware acceleration, such as a field programmable gate array (FPGA) or an application-specific integrated circuit (ASIC), for example, a tensor processing unit (TPU); or a combination of one or more of them. The one or more storage devices may carry processor control code configured to control the one or more processors to perform operations for reinforcement learning. An exemplary embodiment may be a non-volatile disk storage; a non-volatile computer storage, such as flash memory or read only memory (ROM); a volatile computer storage, such as random access memory (RAM); or a combination of one or more of them. The one or more storage devices may carry data and/or code comprising source, object, or executable code in any form of programming language, compiled or interpreted, such as C, or other code such as in a hardware description language. The system may comprise one or more controllers trained by reinforcement learning, for example, to receive observation signals as input and to output action signals. Other hardware components for implementing the various embodiments of the subject matter will be apparent to the skilled person.

The subject matter of the present disclosure provides one or more computer storage media storing instructions that, when executed by one or more computers, cause the one or more computers to perform operations for selecting actions to be performed by an agent that interacts with an environment by receiving observations, in response, performing actions from a set of actions, wherein the observations comprise data from the mapping of applied bacteria, and wherein the actions comprise data for the prescription of a bacterial product. The one or more computer storage media may carry processor control code configured to control the processor of the one or more computers to perform operations for reinforcement learning. An exemplary embodiment may be a non-volatile memory storage, such as a semiconductor memory device, for example, EEPROM or flash memory; a magnetic memory device, for example, hard disk drives; a magneto-optical memory storage; an optical memory storage, for example, a CD-ROM disk; or a combination of one or more of them. Other hardware components for implementing the various embodiments of the subject matter will be apparent to the skilled person.

While operations may be illustrated in the drawings, the description, and the claims by showing a particular order, the disclosure is not limited to the particular order shown, such as a sequential order. Other embodiments and derivations for performing the operations to achieve desirable results are in the scope of the present disclosure, for example, operations may be repeated or parallelized instead of being performed incrementally.

While interaction and communication may be illustrated in the drawings, the description, and the claims by showing a particular direction, the disclosure is not limited to the particular direction shown, such as a single direction. Other embodiments and derivations for directing interaction and communication to achieve desirable results are in the scope of the present disclosure, for example, interaction and communication flows may not be one-to-one directed and multiple flows may be applicable.

While modules and components may be illustrated in the drawings, the description, and the claims by showing a particular arrangement, the disclosure is not limited to the particular arrangement shown, such as a separate arrangement. Other embodiments and derivations for arranging the modules and components to achieve desirable results are in the scope of the present disclosure, for example, multiple modules or components may be integrated into a single module or component and conversely, a single module or component may be split into multiple modules or components.

The various embodiments of the subject matter of the present disclosure may be implemented in software, firmware, hardware, or in a combination of one or more of them. Any feature described in relation to one embodiment may be used alone, may be used in combination with one or more of the other features described in relation to the one embodiment, or may be used in combination with one or more features described in relation to one or more of the other embodiments. Specific implementation details should not be construed as limitations on the scope of the disclosure, but rather as descriptions of features that may be specific to particular embodiments of the subject matter. Further modifications and alternative embodiments are within the scope of the disclosure and the scope of the following claims.

What is claimed is:

1. A system comprising one or more computers and one or more storage devices storing instructions that, when executed by the one or more computers, cause the one or more computers to perform operations for selecting actions to be performed by an agent that interacts with an environment by receiving observations, in response, performing actions from a set of actions, the operations comprising:

receiving, by an actor of one or more actors, an observation, wherein each actor executes on a respective computing unit, wherein each actor is configured to operate on a surface part distinct from operations of each other actor, wherein each actor receives, periodically, a context, wherein the context comprises a bacterial product to be prescribed on the surface part, wherein the observation comprises data from the mapping of applied bacteria on the surface part;

selecting, by the actor, an action to be performed by the agent, wherein the action comprises data for the prescription of the bacterial product on the surface part; and receiving, by the actor, a next observation in response to the action being performed.

2. The system of claim 1, the operations further comprising:

learning, by a learner of one or more learners, a strategy for selecting actions, wherein each learner executes on a respective computing unit, wherein each learner is configured to operate on a surface class distinct from operations of each other learner, wherein the surface class comprises one or more surface parts, wherein each learner interacts with one or more of the actors, wherein each of the one or more of the actors is configured to operate on one of the surface parts of the surface class on which the learner is configured to operate.

3. The system of claim 2, the operations further comprising:
    selecting, periodically, by a p-actor of one or more p-actors, a context, wherein each p-actor executes on a respective computing unit, wherein each p-actor is configured to operate on a surface class distinct from operations of each other p-actor.

4. The system of claim 3, the operations further comprising:
    learning, by a p-learner of one or more p-learners, a strategy for selecting contexts, wherein each p-learner executes on a respective computing unit, wherein each p-learner is configured to operate on a surface group distinct from operations of each other p-learner, wherein the surface group comprises one or more surface classes, wherein each p-learner interacts with one or more of the p-actors, wherein each of the one or more of the p-actors is configured to operate on one of the surface classes of the surface group on which the p-learner is configured to operate.

5. The system of claim 3, wherein one or more of the p-actors are further configured to perform operations, the operations comprising:
    receiving a context preference; and
    processing, prior to selecting the context, the context preference.

6. The system of claim 5, wherein receiving a context preference comprises:
    receiving a context preference signal from one or more physical entities, the physical entities comprising computer-implemented decision support tools, wherein the computer-implemented decision support tools are one or more of a smart device, an IoT device, and a computer device configured to execute one or more programs with at least one user interface for the context preference input.

7. The system of claim 1, wherein one or more of the actors are further configured to perform operations, the operations comprising:
    receiving an action preference; and
    processing, prior to selecting the action, the action preference.

8. The system of claim 7, wherein receiving an action preference comprises:
    receiving an action preference signal from one or more physical entities, the physical entities comprising computer-implemented decision support tools, wherein the computer-implemented decision support tools are one or more of a smart device, an IoT device, and a computer device configured to execute one or more programs with at least one user interface for the action preference input.

9. The system of claim 1, wherein receiving an observation comprises:
    receiving an observation signal from one or more physical entities, the physical entities comprising mapping tools, wherein the mapping tools are one or more of an unmanned aerial vehicle, a smart device, an IoT device, and a robotic device configured to be used for the mapping of applied bacteria on the surface part.

10. The system of claim 1, wherein selecting an action comprises:
    sending an action signal to one or more physical entities, the physical entities comprising prescription tools, wherein the prescription tools are one or more of an unmanned aerial vehicle, a head-mounted display, and a robotic device configured to be used for the prescription of the bacterial product on the surface part.

11. A computer-implemented method for training a reinforcement learning system, the reinforcement learning system selecting actions to be performed by an agent that interacts with an environment by receiving observations, in response, performing actions from a set of actions, the method comprising:

receiving, by an actor of one or more actors, an observation, wherein each actor executes on a respective computing unit, wherein each actor is configured to operate on a surface part distinct from operations of each other actor, wherein each actor receives, periodically, a context, wherein the context comprises a bacterial product to be prescribed on the surface part, wherein the observation comprises data from the mapping of applied bacteria on the surface part;

selecting, by the actor, an action to be performed by the agent, wherein the action comprises data for the prescription of the bacterial product on the surface part; and receiving, by the actor, a next observation in response to the action being performed.

12. The computer-implemented method of claim 11, further comprising:

learning, by a learner of one or more learners, a strategy for selecting actions, wherein each learner executes on a respective computing unit, wherein each learner is configured to operate on a surface class distinct from operations of each other learner, wherein the surface class comprises one or more surface parts, wherein each learner interacts with one or more of the actors, wherein each of the one or more of the actors is configured to operate on one of the surface parts of the surface class on which the learner is configured to operate.

13. The computer-implemented method of claim 12, further comprising:

selecting, periodically, by a p-actor of one or more p-actors, a context, wherein each p-actor executes on a respective computing unit, wherein each p-actor is configured to operate on a surface class distinct from operations of each other p-actor.

14. The computer-implemented method of claim 13, further comprising:

learning, by a p-learner of one or more p-learners, a strategy for selecting contexts, wherein each p-learner executes on a respective computing unit, wherein each p-learner is configured to operate on a surface group distinct from operations of each other p-learner, wherein the surface group comprises one or more surface classes, wherein each p-learner interacts with one or more of the p-actors, wherein each of the one or more of the p-actors is configured to operate on one of the surface classes of the surface group on which the p-learner is configured to operate.

15. One or more computer storage media storing instructions that, when executed by one or more computers, cause the one or more computers to perform operations for selecting actions to be performed by an agent that interacts with an environment by receiving observations, in response, performing actions from a set of actions, the operations comprising:

receiving, by an actor of one or more actors, an observation, wherein each actor executes on a respective computing unit, wherein each actor is configured to operate on a surface part distinct from operations of each other actor, wherein each actor receives, periodically, a context, wherein the context comprises a bacterial product to be prescribed on the surface part, wherein the observation comprises data from the mapping of applied bacteria on the surface part;

selecting, by the actor, an action to be performed by the agent, wherein the action comprises data for the prescription of the bacterial product on the surface part; and receiving, by the actor, a next observation in response to the action being performed.

16. The computer storage media of claim 15, the operations further comprising:

learning, by a learner of one or more learners, a strategy for selecting actions, wherein each learner executes on a respective computing unit, wherein each learner is configured to operate on a surface class distinct from operations of each other learner, wherein the surface class comprises one or more surface parts, wherein each learner interacts with one or more of the actors, wherein each of the one or more of the actors is configured to operate on one of the surface parts of the surface class on which the learner is configured to operate.

17. A computer-implemented method for federated learning a global strategy for selecting actions, wherein the actions comprise data for the prescription of a bacterial product, the method comprising:

receiving, by a federated learner of a plurality of federated learners, a global strategy from a federator;

determining, by the federated learner, a local update to the global strategy; and sending, by the federated learner, the local update to the federator.

18. The computer-implemented method of claim 17, further comprising:

receiving, by the federator, one or more local updates from the plurality of federated learners, wherein each federated learner is configured to operate on a local surface class of the global surface class on which the federator is configured to operate; and determining, by the federator, a global update to the global strategy.

19. The computer-implemented method of claim 18, wherein the global strategy is a neural network that is configured to receive an input comprising an observation, wherein the observation comprises data from the mapping of applied bacteria, and to generate a neural network output from the input in accordance with a set of parameters, wherein federated learning the global strategy comprises updating the values of the set of parameters of the neural network.

20. The computer-implemented method of claim 19, wherein updating the values of the set of parameters of the neural network comprises determining, by the federated learner, the local update to the global strategy based at least in part on a gradient vector, wherein the gradient vector is determined by performing one or more iterations of one or more gradient training techniques on the global strategy with respect to local experience data.

* * * * *